(12) United States Patent
Hareyama

(10) Patent No.: US 11,547,430 B2
(45) Date of Patent: Jan. 10, 2023

(54) ENERGY TREATMENT SYSTEM, CONTROLLER OF POWER SUPPLY TO TREATMENT DEVICE, AND CONTROLLING METHOD OF POWER SUPPLY TO TREATMENT DEVICE

(71) Applicant: OLYMPUS CORPORATION, Hachioji (JP)

(72) Inventor: Norihiko Hareyama, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 839 days.

(21) Appl. No.: 16/290,276

(22) Filed: Mar. 1, 2019

(65) Prior Publication Data

US 2019/0192184 A1    Jun. 27, 2019

Related U.S. Application Data

(63) Continuation of application No. PCT/JP2016/075619, filed on Sep. 1, 2016.

(51) Int. Cl.
*A61B 17/32* (2006.01)
*A61B 17/00* (2006.01)
(Continued)

(52) U.S. Cl.
CPC ........... *A61B 17/320092* (2013.01); *A61B 18/1445* (2013.01); *A61B 2017/0003* (2013.01);
(Continued)

(58) Field of Classification Search
CPC .......... A61B 17/320092; A61B 2017/320094; A61B 17/003
See application file for complete search history.

(56) References Cited

U.S. PATENT DOCUMENTS

2012/0310264 A1* 12/2012 Messerly .............. B06B 1/0284
606/169
2016/0287317 A1   10/2016 Tsubuku et al.

FOREIGN PATENT DOCUMENTS

WO    2015/122306 A1    8/2015
WO    2015/122307 A1    8/2015
(Continued)

OTHER PUBLICATIONS

Tsubuku Yoshihiro, Ultrasonic Treatment Device (Description Translated), Feb. 2, 2015, pp. 1-29 (Year: 2015).*

(Continued)

*Primary Examiner* — Katherine M Shi
*Assistant Examiner* — Mohammed S Adam
(74) *Attorney, Agent, or Firm* — Oliff PLC

(57) ABSTRACT

In an energy treatment system, circuitry temporally detects an electrical property value of an ultrasonic transducer. After an elapse of predetermined time since a power supply outputs electric power by first output power, when determining that the value has started gradual decrease, causes the power supply to change the electric power from the first output power to second output power smaller than the first output power, and after the change to the second output power, when the electrical property has gradually increased, causes the power supply to change the electric power from the second output power to third output power larger than the second output power.

13 Claims, 8 Drawing Sheets

(51) Int. Cl.
  *A61B 18/00* (2006.01)
  *A61B 18/14* (2006.01)
(52) U.S. Cl.
  CPC ............... *A61B 2017/00022* (2013.01); *A61B 2017/320082* (2017.08); *A61B 2017/320094* (2017.08); *A61B 2017/320095* (2017.08); *A61B 2018/00702* (2013.01)

(56) References Cited

FOREIGN PATENT DOCUMENTS

| WO | 2015/122309 A1 | 8/2015 | |
|---|---|---|---|
| WO | WO-2015122309 A1 * | 8/2015 | ..... A61B 17/320092 |
| WO | 2016/013338 A1 | 1/2016 | |

OTHER PUBLICATIONS

Mar. 5, 2019 International Preliminary Report on Patentability issued in International Patent Application No. PCT/JP2016/075619.

Dec. 6, 2016 International Search Report issued in International Patent Application No. PCT/JP2016/075619.

* cited by examiner

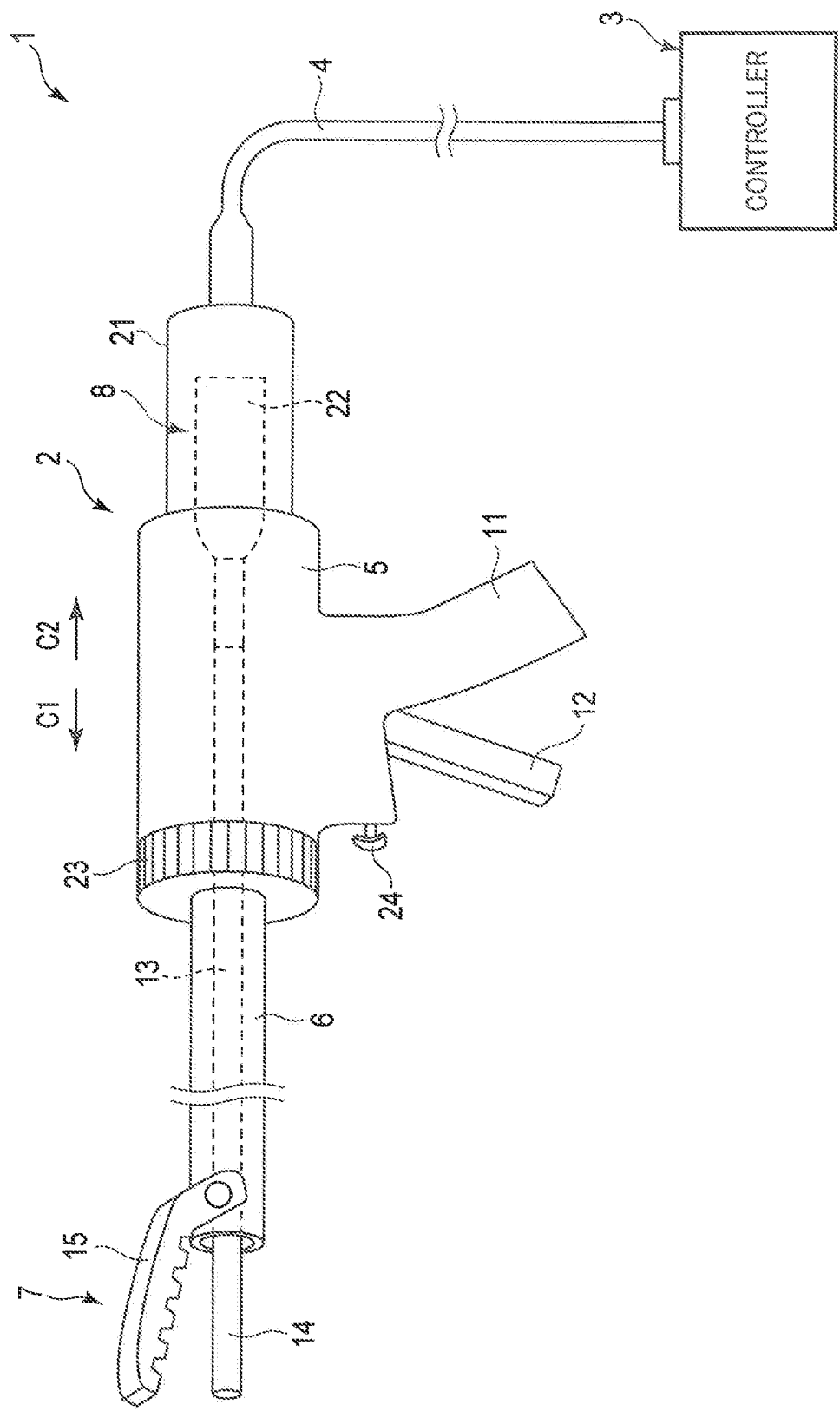
F I G. 1

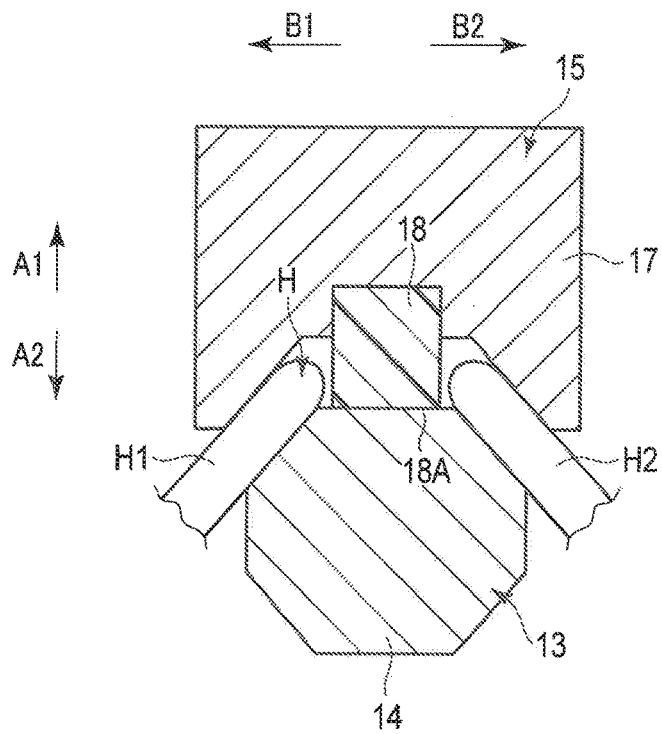
F I G. 4
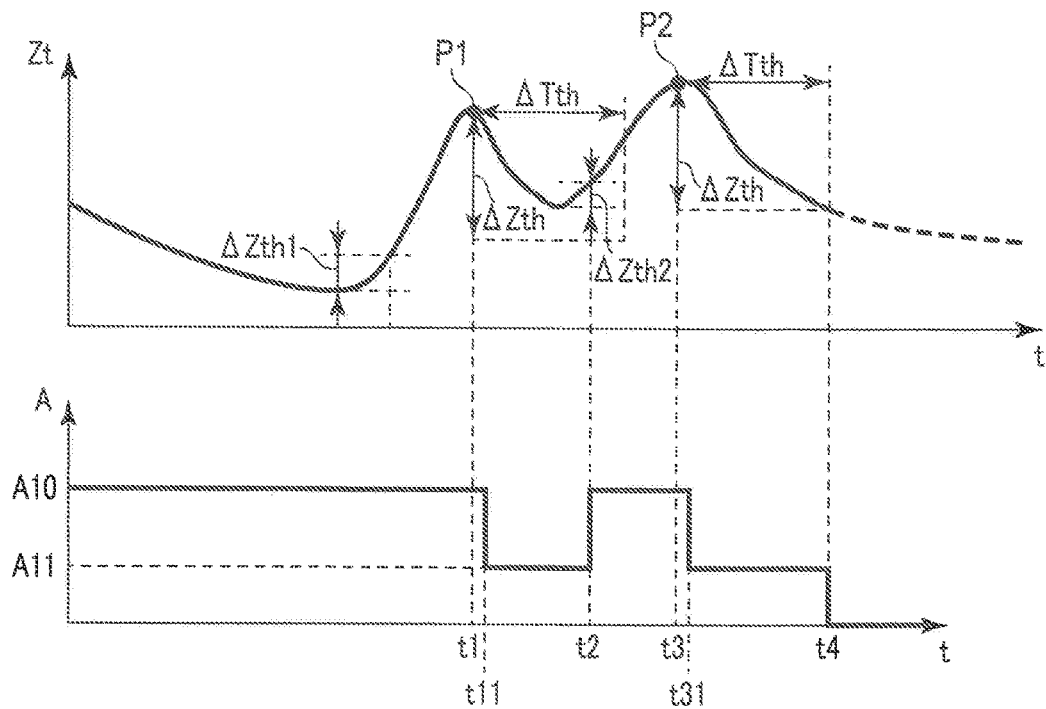
F I G. 5

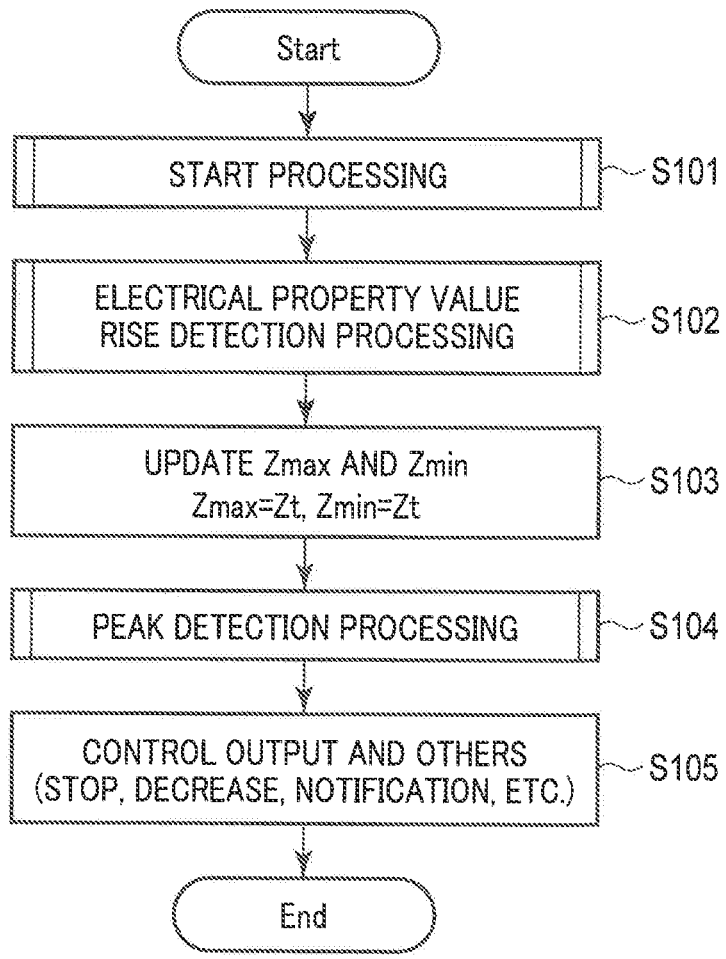
F I G. 6

ENERGY TREATMENT SYSTEM, CONTROLLER OF POWER SUPPLY TO TREATMENT DEVICE, AND CONTROLLING METHOD OF POWER SUPPLY TO TREATMENT DEVICE

CROSS-REFERENCE TO RELATED APPLICATIONS

This application is a Continuation Application of PCT Application No. PCT/JP2016/075619, filed Sep. 1, 2016, the entire contents of which are incorporated herein by references.

BACKGROUND OF THE INVENTION

1. Field of the Invention

The present invention relates to an energy treatment system that treats a treatment target by using ultrasonic vibration, controller of power supply to treatment device, and controlling method of power supply to treatment device.

2. Description of the Related Art

There is known an energy treatment system that has an ultrasonic treatment device performing treatment such as coagulation or incision of a treatment target by using ultrasonic vibration energy.

For example, each of WO2015/122306 and WO2015/122307 discloses an ultrasonic treatment system having an ultrasonic treatment device with an ultrasonic transducer and a controller with a power supply. The ultrasonic treatment device has a first gripping piece and a second gripping piece. In this system, when electric power is supplied from the power supply to the ultrasonic transducer, the ultrasonic transducer generates ultrasonic vibration that is transferred to the first gripping piece. When the ultrasonic vibration is transferred to the first gripping piece while the treatment target is gripped between the first gripping piece and the second gripping piece, frictional heat is generated between the first gripping piece and the treatment target. By this frictional heat, the treatment target is coagulated and incised at the same time. In this system, the controller detects temporal changes in electric impedance (ultrasonic impedance) of the ultrasonic transducer during the treatment and determines a peak in the changes, thereby detecting completion of incision of the treatment target.

BRIEF SUMMARY OF THE INVENTION

According to an embodiment of the present invention, an energy treatment system is provided. The energy treatment system comprises a power supply configured to output electric power, an ultrasonic transducer configured to generate ultrasonic vibration by the electric power from the power supply, a first gripping piece to which the ultrasonic vibration generated by the ultrasonic transducer is transferred and that is configured to perform a treatment on a treatment target using the ultrasonic vibration, a second gripping piece that is opened and closed to the first gripping piece, and circuitry configured to temporally detect an electrical property value of the ultrasonic transducer, determining that, after an elapse of predetermined time since the power supply outputs the electric power by first output power, the electrical property value has started gradual decrease, and after determining that the electrical property value has started gradual decrease, the electrical property value gradually increase, and when determining that the electrical property value has started gradual decrease, causes the power supply to change the electric power from the first output power to second output power smaller than the first output power, and after the change to the second output power, when determining that the electrical property value has gradually increased, causes the power supply to change the electric power from the second output voltage to third output voltage larger than the second output voltage.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram illustrating an example of an energy treatment system according to an embodiment of the present invention.

FIG. 4 is a transverse cross-sectional view of an end effector when a treatment target is cut and divided and the treatment target being cut and divided.

FIG. 5 is a diagram illustrating an example of temporal changes in ultrasonic impedance during treatment and an example of temporal changes in amplitude of a first gripping piece vibrating due to ultrasonic vibration.

FIG. 6 is a flowchart of an example of processing by a processor during treatment by the energy treatment system.

DETAILED DESCRIPTION

Figure 2:
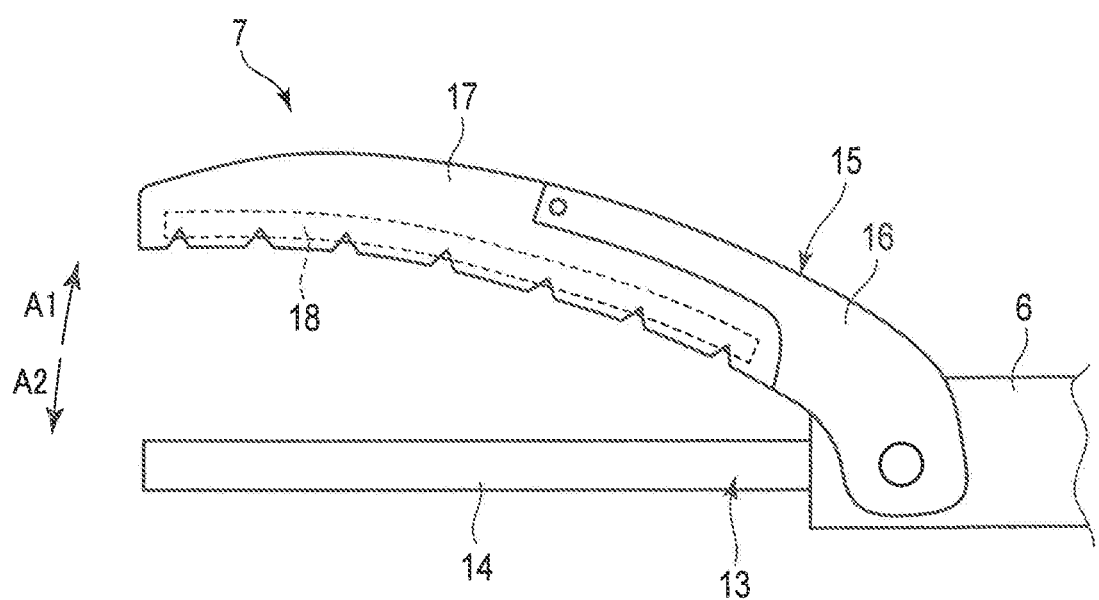
FIG. 2 is a schematic diagram illustrating a distal end portion of an ultrasonic treatment device.

FIG. 1 is a schematic diagram illustrating an example of an energy treatment system according to an embodiment of the present invention. An energy treatment system 1 has an ultrasonic treatment device 2 and a controller 3. The energy treatment system 1 is configured to perform treatment such as coagulation or incision of a treatment target (for example, body tissue) by using ultrasonic vibration. The ultrasonic treatment device 2 is a handpiece to be gripped by an operator and is a surgical energy device capable of outputting ultrasonic vibration energy. The ultrasonic treatment device 2 is attachably and detachably connected to the controller 3 by a cable 4.

The ultrasonic treatment device 2 has a housing 5, a sheath 6 distally coupled to the housing 5 (as seen in a direction indicated by arrow C1 in FIG. 1), an end effector 7 provided at the distal end portion of the sheath 6, and a transducer unit 8 proximally coupled to the housing 5 (as seen in a direction indicated by arrow 2 in FIG. 1). The housing 5 is provided with a fixed handle 11. The housing 5 also has a movable handle 12 attached in a rotatable manner. When the movable handle 12 rotates with respect to the housing 5, the movable handle 12 is opened or closed to the fixed handle 11.

In the ultrasonic treatment device 2, a rod (probe) 13 extends in a direction toward the distal end passing from the inside of the housing 5 to the inside of the sheath 6. The rod 13 is made from a material with high vibration transmissibility such as 64 titanium (Ti-6Al-4V).

FIG. 2 is a schematic diagram illustrating a distal end portion of the ultrasonic treatment device 2. The distal end portion of the rod 13 constitutes a first gripping piece 14. The rod 13 is inserted into the sheath 6 such that the first gripping piece 14 protrudes from the distal end of the sheath 6. A second gripping piece (jaw) 15 is rotatably attached to the distal end portion of the sheath 6. The first gripping piece 14 and the second gripping piece 15 constitute the end effector 7 that performs treatment such as coagulation or incision of a treatment target in a direction toward the distal end of the ultrasonic treatment device 2.

In the inside of the sheath 6, a movable member not illustrated which coupling the second gripping piece 15 and the movable handle 12 extends in a direction from the proximal end to the distal end. When the movable handle 12 is opened or closed to the fixed handle 11, the movable member moves to a direction toward the proximal end or a direction toward the distal end. Accordingly, the second gripping piece 15 rotates with respect to the sheath 6, and the second gripping piece 15 is opened or closed to the first gripping piece 14. That is, the second gripping piece 15 moves in directions indicated by arrows A1 and A2 in FIG. 2.

The second gripping piece 15 has a jaw main body 16 with a proximal end portion attached to the sheath 6, a holder 17 attached to the jaw main body 16, and a pad 18 attached to the holder 17. The jaw main body 16 and the holder 17 are made from an electrically conductive metal, for example. The pad 18 is made from a fluorine resin such as polytetrafluoroethylene (PTFE) and has electrical insulation properties. While there is no space between the first gripping piece 14 and the second gripping piece 15, the pad 18 is in abutment with the first gripping piece 14. While the pad 18 is in abutment with the first gripping piece 14, no other than the pad 18 in the second gripping piece 15 are in abutment with the first gripping piece 14.

Returning to FIG. 1, the transducer unit 8 has a transducer case 21 and an ultrasonic transducer 22 provided in the transducer case 21. The ultrasonic transducer 22 extends from the inside of the transducer case 21 to the inside of the housing 5 and is proximally connected to the rod 13 in the housing 5. One end of the cable 4 is connected to the transducer case 21. The other end of the cable 4 is attachably and detachably connected to the controller 3. Alternatively, the transducer case 21 may not be provided such that the ultrasonic transducer 22 is disposed in the housing 5. In this case, one end of the cable 4 is connected to the housing 5.

A rotatable knob 23 is attached to the housing 5. When the rotatable knob 23 is rotated, the sheath 6, the rod 13 including the first gripping piece 14, the second gripping niece 15, and the ultrasonic transducer 22 rotate together with the rotatable knob 23 around a central axis of the sheath 6 with respect to the housing 5. Accordingly, the angle of the end effector 7 around the central axis of the sheath 6 is adjusted. The rotatable knob 23 may not be provided.

The housing 5 is provided with an operation button 24. The operation button 24 is used to input an operation of supplying electric energy for generating ultrasonic vibration in the ultrasonic transducer 22 from the controller 3. Instead of the operation button 24 or in addition to the operation button 24, a foot switch (not illustrated) separately from the ultrasonic treatment device 2 may be provided.

Figure 3:
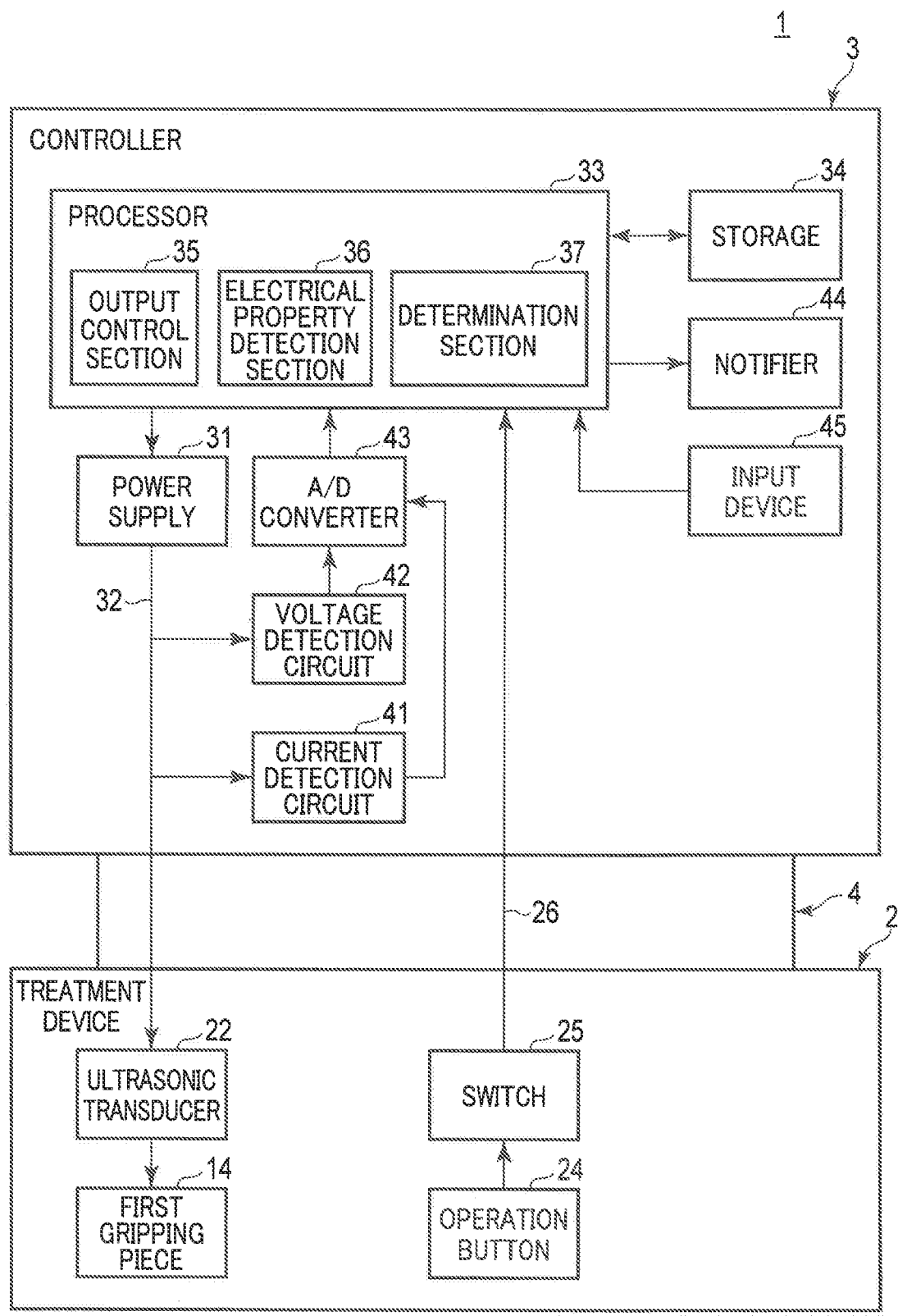
FIG. 3 is a schematic block diagram illustrating an example of the energy treatment system.

FIG. 3 is a schematic block diagram illustrating an example of the energy treatment system 1. The controller 3 has a power supply 31. The power supply 31 is electrically connected to the ultrasonic transducer 22 via an electrical path 32 extending through the cable 4. The power supply 31 has a conversion circuit or the like that converts electric power from a battery power supply or an electric outlet into electric energy to be supplied to the ultrasonic transducer 22. The power supply 31 outputs the electric energy converted by the conversion circuit. The electric energy output from the power supply 31 is supplied to the ultrasonic transducer 22 via the electrical path 32. In this manner, the power supply 31 is an ultrasonic power output unit that supplies electric energy for generation of ultrasonic vibration in the ultrasonic transducer 22, that is, outputs electric power for generating vibration to the ultrasonic transducer 22.

The controller 3 has a processor (controller) 33 that controls the entire energy treatment system 1 and a storage 34. The processor 33 is formed from an integrated circuit including a central processing unit (CPU), an application specific integrated circuit (ASIC), or a field programmable gate array (FPGA). The processor 33 may be formed from one integrated circuit or a plurality of integrated circuits. The controller 3 may be provided with one processor 33 or a plurality of separate processors 33. The processor 33 performs processing according to a program stored in the processor 33 or the storage 34. The storage 34 stores processing programs to be used by the processor 33 and parameters and tables to be used in operations by the processor 33.

The ultrasonic treatment device 2 has a switch 25. The switch 25 operates in conjunction with an operation by the operation button 24 and is electrically connected to the processor 33 via an electrical path 26 extending through the cable 4. The switch 25 is provided in a detection circuit, for example, and is switched based on an input into the operation button 24. Specifically, the switch 25 is turned from OFF state to ON state by an operation input from the operation button 24. According to the turning of the switch 25 into the ON state, the processor 33 detects that an operation is input into the operation button 24.

The processor 33 has an output control section 35. The output control section 35 controls output of vibration generation power from the power supply 31 based on an electrical signal transferred from the switch 25 by an input into the operation button 24, for example. When the electric energy is supplied from the power supply 31 to the ultrasonic transducer 22 based on the control signal from the output control section 35, an alternating-current voltage applied from an electrode not illustrated in the ultrasonic transducer 22 to a piezoelectric element is converted into ultrasonic vibration, and thus ultrasonic vibration is generated in the ultrasonic transducer 22. The generated ultrasonic vibration is transferred in a direction from the proximal end to the distal end through the rod 13. Then, the rod 13 including the first gripping piece 14 makes ultrasonic vibration. The ultrasonic treatment device 2 uses the ultrasonic vibration transferred to the first gripping piece 14 to perform treatment on the treatment target.

The controller 3 has a current detection circuit 41, a voltage detection circuit 42, and an analog/digital (A/D) converter 43. The current detection circuit 41 detects output current from the power supply 31 to the ultrasonic transducer 22. The voltage detection circuit 42 detects output voltage from the power supply 31 to the ultrasonic transducer 22. Transmitted to the A/D converter 43 are an analog signal indicating the current value detected by the current detection circuit 41 and an analog signal indicating the voltage value detected by the voltage detection circuit 42. The A/D converter 43 converts the received analog signal into a digital signal and transmits the same to the processor 33.

The processor 33 has an electrical property detection section 36. The electrical property detection section 36 (hereinafter, called property detection section 36) is a detection circuit, for example, that detects temporally an electrical property value of the ultrasonic transducer 22 based on signals of an output current and an output voltage received from the A/D converter 43. The electrical property value here refers to any of an electric impedance value of the ultrasonic transducer 22, a value of voltage applied to the ultrasonic transducer 22, a value of power supplied to the ultrasonic transducer 22, and others. The property detection section 36 detects (calculates) the electric impedance value, the voltage value, the power value, or the like of the ultrasonic transducer 22 as property value relating to the electric energy output from the power supply 31 to the ultrasonic transducer 22. The following description is based on the assumption that the property detection section 36 detects the electric impedance value of the ultrasonic transducer 22 as electrical property value. However, the voltage value or the power value can also be used as electrical property value as described above. The electric impedance of the ultrasonic transducer 22 is herein called as "ultrasonic impedance".

The processor 33 has a determination section 37. The determination section 37 is a determination circuit, for example, that makes a determination on ultrasonic output control based on the electrical property value or the like detected by the property detection section 36. The output control section 35 controls output of the power supply 31 based on the result of determination by the determination section 37.

In the present embodiment, while the electric energy is supplied from the power supply 31 to the ultrasonic transducer 22, the output control section 35 controls output of the electric energy from the power supply 31 by constant current control under which the value of the output current is temporally kept constant. In this case, the output voltage from the power supply 31 is adjusted in response to a change in the ultrasonic impedance value. Specifically, as the ultrasonic impedance increases, the output voltage is raised so that the value of the output current is temporally kept constant. At this time, the output power also increases in response to the rise in the output voltage. In reverse, as the ultrasonic impedance decreases, the output voltage is lowered so that the value of the output current is temporally kept constant. At this time, the output power also decreases in response to the reduction in the output voltage.

The controller 3 has a notifier 44. The processor 33 includes a notification control section that controls the operation of the notifier 44 based on the result of determination by the determination section 37. The notifier 44 makes a notification to the user or the like by an acoustic notification such as a notification sound or the like from a beeper, a visual notification such as illumination or flickering of light or display of text or the like on a screen, or a combination of the foregoing notifications. The output control section 35 and the notification control section act as an output control section in the processor 33.

The controller 3 has an input device 45 that receives an instruction from an operator as a user. The input device 45 is a touch panel, a keyboard, or the like. A user interface not illustrated sets various parameters stored in the storage 34 by an input operation from the input device 45 or switches between ON and OFF states of various functions of the ultrasonic treatment device 2, that is, switches between the kinds of operations or between the enabling and disabling of an operation.

Next, an operation for performing a treatment on a treatment target using the energy treatment system 1 will be described. First, the operator grips the fixed handle 11 and the movable handle 12 of the ultrasonic treatment device 2. The operator then disposes the treatment target between the first gripping piece 14 and the second gripping piece 15 and closes the movable handle 12 to the fixed handle 11. Accordingly, the second gripping piece 15 is closed to the first gripping piece 14, and the treatment target is held between the first gripping piece 14 and the second gripping piece 15. The operator makes an operation input by the operation button 24. Accordingly, the switch 25 is turned to the ON state and the processor 33 detects the operation input from the operation button 24.

When the operation input from the operation button 24 is detected, the output control section 35 of the processor 33 causes the power supply 31 to output electric energy to the ultrasonic transducer 22. Accordingly, the ultrasonic transducer 22 generates ultrasonic vibration that is transferred to the first gripping piece 14 through the rod 13. When the ultrasonic vibration is transferred to the first gripping piece 14 while the treatment target is gripped between the first gripping piece 14 and the second gripping piece 15, frictional heat is generated between the first gripping piece 14 and the treatment target. By this frictional heat, the treatment target is coagulated and incised at the same time.

FIG. 4 is a transverse cross-sectional view of the end effector 7 when a treatment target is incised and the treatment target H being incised. At the treatment using the ultrasonic treatment device 2, the treatment target H gripped between the gripping pieces 14 and 15 is divided in width directions of the end effector 7 (the width directions refers to directions indicated by arrows B1 and B2 in FIG. 4). The phenomenon that the treatment target H is divided in the width directions of the end effector 7 is called herein "cut and division". As illustrated in FIG. 4, the treatment target H is divided into a cut and divided portion H1 and a cut and divided portion H2 in the width directions of the end effector 7. A gripping surface 18A of the pad 18 in the second gripping piece 15 comes into contact with the first gripping piece 14 between the cut and divided portions H1 and H2.

When the first gripping piece 14 vibrates due to ultrasonic vibration while the gripping surface 18A of the pad 18 is in contact with the first gripping piece 14, the gripping surface 18A becomes worn or deformed due to frictional heat. Therefore, during treatment, the excessive vibration of the first gripping piece 14 should be avoided while the gripping surface 18A is in contact with the first gripping piece 14.

Next, an outline of behavior of ultrasonic impedance during treatment will be described. During treatment, after the start of ultrasonic output, the ultrasonic impedance decreases once and then becomes stabled. The ultrasonic impedance decreases once because a moisture content of body tissue evaporates and protein denaturation starts in the body tissue, for example.

After that, when the treatment target is being incised while being coagulated by ultrasonic vibration, the ultrasonic impedance gradually increases until the incision of the treatment target gripped between the gripping pieces 14 and 15 is started. This is because, after protein denaturation in body tissue, the body tissue becomes coagulated and hardened to increase the frictional coefficient between the first gripping piece 14 and the body tissue increases, for example. This is also because, as illustrated in. FIG. 4, for example, the first gripping piece 14 comes into contact with the pad 18 of the second gripping piece 15 to increase the frictional coefficient between the gripping pieces 14 and 15. The "gradual increase" here means that the ultrasonic impedance gradually increases with the progress of a time t, which includes the state that the ultrasonic impedance gradually increases with minute increases and decreases of several tens $\Omega$ or increases and decreases of more than 100$\Omega$, for example.

After the incision of the gripped treatment target is started, ultrasonic impedance Zt gradually decreases. This is because, with the progress of the incision, the second gripping piece 15 is being closed to the first gripping piece 14 to decrease the amount of gripping force, for example. This is because the wear in the pad 18 of the second gripping piece 15 comes to a stabled state to decrease the frictional coefficient between the gripping pieces 14 and 15, for example. The "gradual decrease" here means that the ultrasonic impedance gradually decreases with the progress of a time t, which includes the state that the ultrasonic impedance gradually decreases with, minute increases and decreases of several tens $\Omega$ or decreases and decreases of more than 100$\Omega$, for example.

Therefore, it is possible to detect that the treatment target has been cut and divided, that is, the incision of the treatment target has completed, by detecting temporal changes in the ultrasonic impedance during treatment by the processor 33 of the controller 3. Although the behavior of the ultrasonic impedance is described here, it is possible to detect that the treatment target has been cut and divided in the same manner by using temporal changes in the electrical property value such as the voltage applied from the power supply 31 to the ultrasonic transducer 22 or the electric power supplied from the power supply 31 to the ultrasonic transducer 22 instead of the ultrasonic impedance.

However, in the case of making an incision in thick or hard body tissue such as a thick blood vessel or cervix uteri or making an incision in body tissue while slowly gripping the fixed handle 11 and the movable handle 12 of the ultrasonic treatment device 2 by the operator, the body tissue gripped between the gripping pieces 14 and 15 is incised not at once but in a stepwise manner. Accordingly, in the foregoing cases, temporal changes in the electrical property value may become complicated with a plurality of peaks.

FIG. 5 is a diagram illustrating an example of temporal changes in ultrasonic impedance during treatment as an example of an electrical property value during treatment, and an example of temporal changes in amplitude of the first gripping piece 14 vibrating due to ultrasonic vibration. In FIG. 5, t represents time, Zt represents ultrasonic impedance at time t, and A represents the amplitude of ultrasonic vibration of the first gripping piece 14.

Until the treatment target gripped between the gripping pieces 14 and 15 is partially cut and divided, the opening angle between the gripping pieces 14 and 15 decreases due to the incision. In the treatment target, and be pressing force from the second gripping piece 15 to the first gripping piece 14 becomes gradually small due to state changes in the treatment target and the like. Accordingly, the load on the rod 13 becomes gradually small. Therefore, the ultrasonic impedance gradually decreases until the treatment target is partially cut and divided and the pad 18 comes into contact with the first gripping piece 14. This is the gradual decrease of the ultrasonic impedance after a first peak P1 illustrated in FIG. 5, for example.

When the treatment target is partially cut and divided, the pad 18 comes into contact with the first gripping piece 14 at the cut and divided portion. When part of the pad 18 starts to contact the first gripping piece 14, the load on the rod 13 becomes gradually large until the treatment target is entirely cut and divided and the pad 18 contacts the first gripping piece 14 at the approximately entire length. Therefore, after the treatment target is partially cut and divided, the ultrasonic impedance gradually increases. This is the gradual increase of the ultrasonic impedance toward a second peak P2 illustrated in FIG. 5, for example.

Then, when the treatment target is entirely cut and divided, the pad 18 contacts the first gripping piece 14 at the approximately entire length. After the pad 18 contact the first gripping piece 14 by the approximately entire length, the opening angle between the gripping pieces 14 and 15 hardly changes. In addition, when the pad 18 contacts the first gripping piece 14 at the approximately entire length, a portion of contact between the pad 18 and the first gripping piece 14 starts to be worn or melted by frictional heat resulting from the ultrasonic vibration, and thus the load on the rod 13 becomes gradually small. Therefore, after the treatment target is entirely cut and divided, the ultrasonic impedance gradually decreases. This is the gradual decrease of the ultrasonic impedance after the second peak P2 illustrated in FIG. 5, for example, As described above, the electrical property values including ultrasonic impedance, voltage, and electric power, in this case, the ultrasonic impedance becomes stabled after the start of output, gradually increases, reaches the first peak P1, and then gradually decreases. The body tissue as treatment target is partially incised on a surface of contact with the first gripping piece 14 or the second gripping piece 15 but is not completely cut and divided at a time t1 as a point in time at the first peak P1 of the ultrasonic impedance. At this time, part of the gripping surface 18A of the pad 18 of the second gripping piece 15 is already in contact with the body tissue. After the first peak P1, the ultrasonic impedance gradually decreases and turns to gradual increase again, and then reaches the second peak P2. Then, the body tissue is completely cut and divided at a time t3 as a point in time at the second peak P2.

In this case, it is assumed, for example, that the determination section 37 of the processor 33 determines that the treatment target has been cut and divided based on the elapse of specified time after the detection of the first peak P1 of the ultrasonic impedance, and the output control section 35 of the processor 33 decreases the output of vibration generation power from the power supply and the subsequent treatment is performed with the decreased output. Accordingly, since part of the treatment target has not yet been cut and divided in actuality, the treatment target will be incised with lowered incision performance of the ultrasonic treatment device 2 after the time when the output was decreased.

In addition, it is assumed that the determination section 37 of the processor 33 determines that the treatment target has been cut and divided based on the elapse of specified time after the detection of the first peak P1 of the ultrasonic impedance, and the output control section 35 of the processor 33 stops the output of the vibration generation power from the power supply 31. Accordingly, although part of the treatment target has not yet been cut and divided in actuality, the supply of the electric energy from the power supply 31 is stopped without completion of appropriate processing, that is, with part of the treatment target yet to be cut and divided.

In addition, in a case where the ultrasonic impedance shows a single peak, for example, the determination section 37 of the processor 33 determines that the treatment target has been cut and divided based on the elapse of specified time after the detection of the peak P1 of the ultrasonic impedance, and the output control section 35 of the processor 33 causes the power supply 31 to stop the output of the vibration generation power. Accordingly, there is a possibility that idle oscillation is generated during the specified time to raise excessively the temperature of the first gripping piece 14 vibrating due to the ultrasonic vibration.

Figure 7:
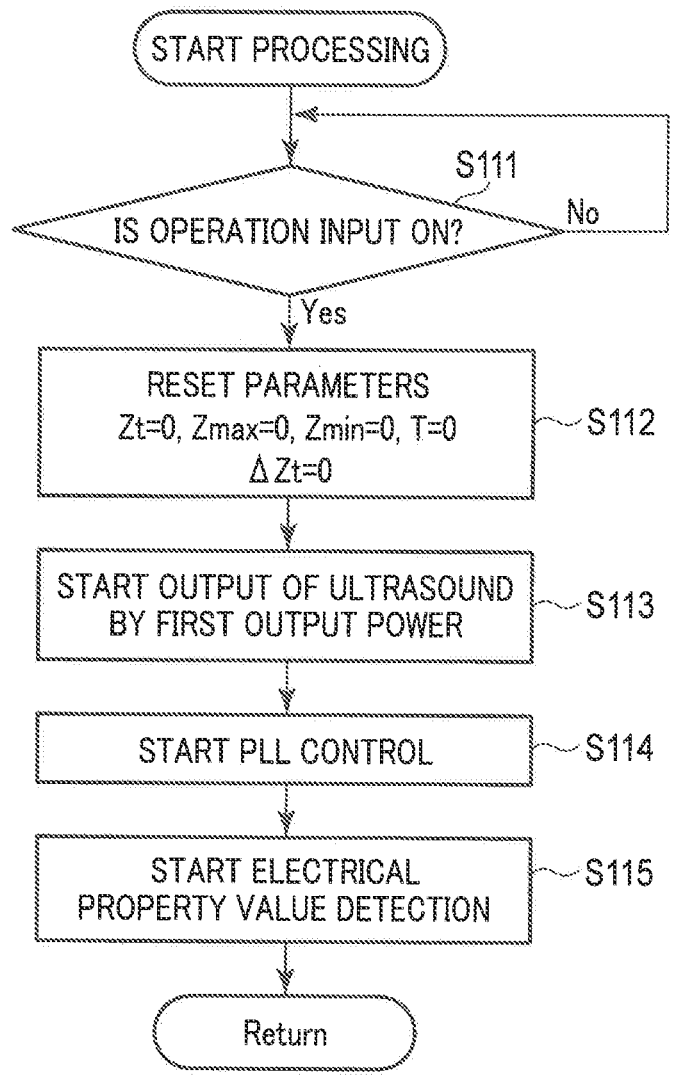
FIG. 7 is a flowchart of an example of start processing.

In light of the foregoing matter, a flow of treatment bar the energy treatment system 1, that is, processing performed by the processor 33 of the controller 3 in the present embodiment will be described. FIG. 6 is a flowchart of an example of processing by the processor 33 during treatment by the energy treatment system 1. The processor 33 first performs start processing (step S101). FIG. 7 is a flowchart of an example of start processing.

In the start processing, the processor 33 determines whether an operation input has been made from the operation button 24, that is, an operation input from the operation button 24 is ON or OFF based on whether the switch 25 is in the ON state (step S111). When no operation input has been made (No), the process returns to step S111. That is, the processor 33 waits until an operation input is made from the operation button 24. When an operation input has been made (Yes), the processor 33 resets the ultrasonic impedance Zt as a parameter for determination, a maximum value Zmax of the ultrasonic impedance, a minimum value Zmin of the ultrasonic impedance, count time T, and an amount of change ΔZt from the peak value of the ultrasonic impedance (Zt=0, Zmax=0, Zmin=0, T=0, ΔZt=0) (step S112).

After step S112, the output control section 35 causes the power supply 31 to start output of electric energy to the ultrasonic transducer 22 by the first output power (step S113). After the output is started, when a predetermined condition is satisfied, a phase locked loop (PLL) control is started (step S114). Under the PLL control, the frequency of the output of the electric energy from the power supply 31 is adjusted such that a phase difference between the output current and the output voltage is smaller than a predetermined threshold. That the output frequency of the power supply 31 is adjusted to match the resonant frequency of a vibrometer. When the PLL control is started, the property detection section 36 starts detection of the ultrasonic impedance as electrical property value with a lock-in (ultrasonic resonant frequency search completion) signal as a trigger (step S115). After step S115, the start processing is terminated, and the process moves to step S102.

After the start of the PLL control, the output control section 35 controls the output power from the power supply 31 by the constant current control as described above under which the value of the output current is temporally kept constant. When the value of the output current is temporally kept constant, the amplitude and vibration speed of the ultrasound generated in the ultrasonic transducer 22 also become temporally approximately constant, and the amplitude and vibration speed of the ultrasound in the first gripping piece 14 also become temporally approximately constant. That is, amplitude A of the ultrasonic vibration of the first gripping piece 14 becomes approximately constant at a relatively high level as illustrated in the part before the time t1 in FIG. 5.

Figure 8:
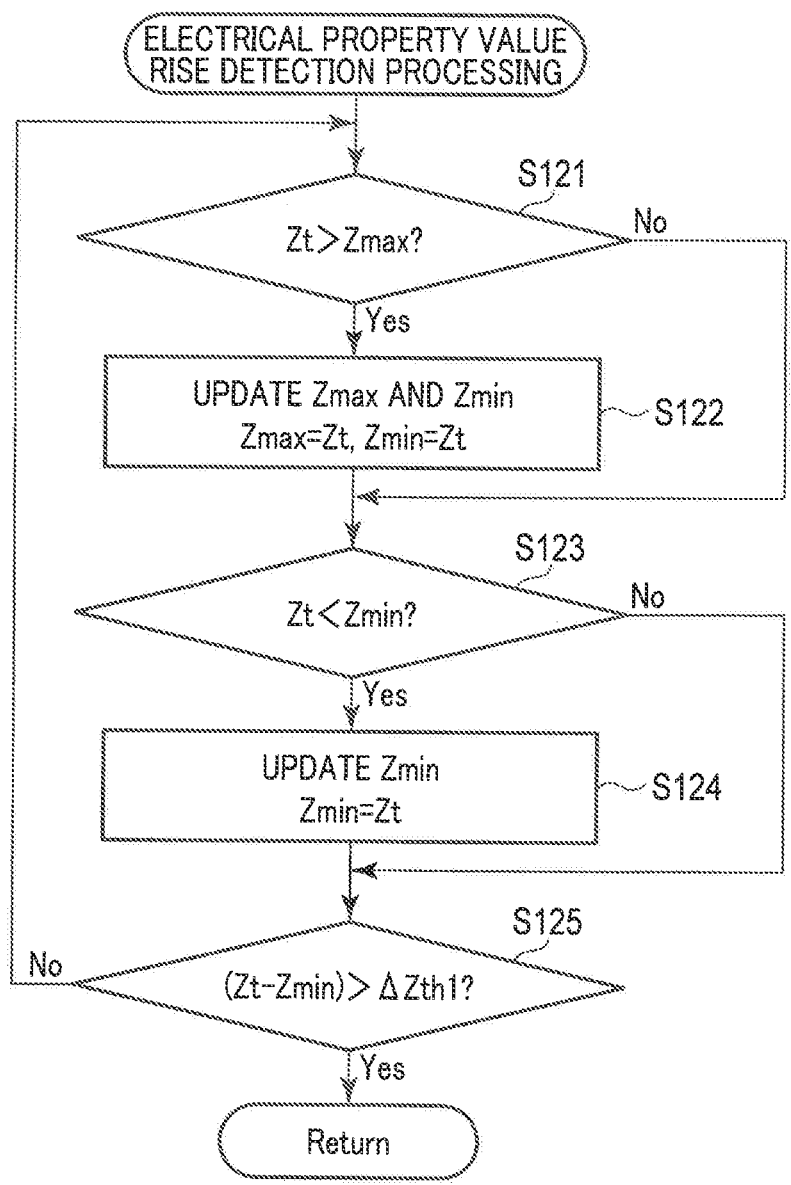
FIG. 8 is a flowchart of an example of ultrasonic impedance rise detection processing.

In this case, after the start of detection of the electrical property value as ultrasonic impedance, the processor 33 performs ultrasonic impedance rise detection processing (step S102). FIG. 8 is a flowchart of an example of rise detection processing.

In step S121, the determination section 37 of the processor 33 determines whether the ultrasonic impedance Zt is larger than the maximum value Zmax of the ultrasonic impedance. When it is determined that the ultrasonic impedance Zt is larger than the maximum value Zmax (Yes), the processor 33 updates the maximum value Zmax of the ultrasonic impedance to the ultrasonic impedance Zt detected by the property detection section 36 (Zmax=Zt), and updates the minimum value Zmin of the ultrasonic impedance to the ultrasonic impedance Zt detected by the property detection section 36 (step S122). Then, the process moves to step S123. On the other hand, when it is determined that the ultrasonic impedance Zt is equal to or less than the maximum value Zmax (No), the process moves to step S123. In this manner, when the ultrasonic impedance Zt is larger than the maximum value Zmax of the ultrasonic impedance, the maximum value Zmax and the minimum value Zmin are updated, and when it is not so, the maximum value Zmax and the minimum value Zmin are not updated.

In step S123, the determination section 37 of the processor 33 determines whether the ultrasonic impedance Zt is smaller than the minimum value Zmin of the ultrasonic impedance. When it is determined that the ultrasonic impedance Zt is smaller than the minimum value Zmin (Yes), the processor 33 updates the minimum value Zmin of the ultrasonic impedance to the ultrasonic impedance Zt detected by the property detection section 36 (Zmin=Zt) (step S124). Then, the process moves to step S125. On the other hand, when it is determined that the ultrasonic impedance Zt is equal to or more than the minimum value Zmin (No), the process moves to step S125. In this manner, when the ultrasonic impedance Zt is smaller than the minimum value Zmin of the ultrasonic impedance, the maximum value Zmax remains unchanged and the minimum value Zmin is updated, and when it is not the maximum value Zmax and the minimum value Zmin are not updated.

In step S125, the determination section 37 of the processor 33 determines whether a gradually increasing value of the ultrasonic impedance Zt from the minimum value Zmin of the ultrasonic impedance, that is, Zt-Zmin is larger than a threshold ΔZth1 as rise detection threshold of the ultrasonic impedance (for example, as illustrated in FIG. 5).

The threshold ΔZth1 may be a prescribed value stored in advance in the storage 34. The described value can be set to each model of the ultrasonic treatment device 2, for example. For example the ultrasonic treatment device 2 has a storage not illustrated in which identification information of the ultrasonic treatment device 2 is stored. The identification information refers to information, for identifying the model (model number) of the ultrasonic treatment device 2, for example, and may be the serial number of the ultrasonic treatment device 2. When, the ultrasonic treatment device 2 is connected to the controller 3 via the cable 4, the processor 33 reads the identification information from the storage in the ultrasonic treatment device 2. The processor 33 specifies the model of the ultrasonic treatment device 2 based on the read identification information, and reads the value of the threshold ΔZth1 and sets the same. Alternatively, the ultrasonic treatment device 2 may have a storage not illustrated in which the threshold ΔZth1 corresponding to the model of the ultrasonic treatment device 2 is stored. In this case, when the ultrasonic treatment device 2 is connected to the controller 3 via the cable 4, the processor 33 reads the threshold ΔZth1 from the storage in the ultrasonic treatment device 2 and sets the same. Alternatively, the threshold ΔZth1 may be set by an operator making an input from the input device 53 based on a temporal change in the ultrasonic impedance.

In step S125, when the determination section 37 of the processor 33 determines that the gradually increasing value Zt-Zmin is equal to or less than the threshold ΔZth1 (No), the process returns to step S121. Specifically, the processor 33 waits for the ultrasonic impedance to increase beyond the set value ΔZth1 while repeatedly performing step S121 and the subsequent steps until the determination section 37 determines that the gradually increasing value Zt-Zmin is larger than the threshold ΔZth1. On the other hand, when the determination section 37 of the processor 33 determines that the gradually increasing value Zt-Zmin is larger than the threshold ΔZth1 (Yes), the processor 33 detects that the ultrasonic impedance has risen beyond the set value ΔZth1, and the process returns to the main flow. Then, the process moves to next step S103.

After step S102, the processor 33 updates the maximum value Zmax of the ultrasonic impedance to the ultrasonic impedance Zt detected by the property detection section 36 (Zmax=Zt), and updates the minimum value Zmin of the ultrasonic impedance to the ultrasonic impedance Zt detected by the property detection section 36 (step S103). That is, when the determination section 37 of the processor 33 determines that the ultrasonic impedance has risen from the minimum value Zmin beyond the set value, the processor 33 sets the value of the ultrasonic impedance Zt to the maximum value Zmax and the minimum value Zmin.

Figure 9:
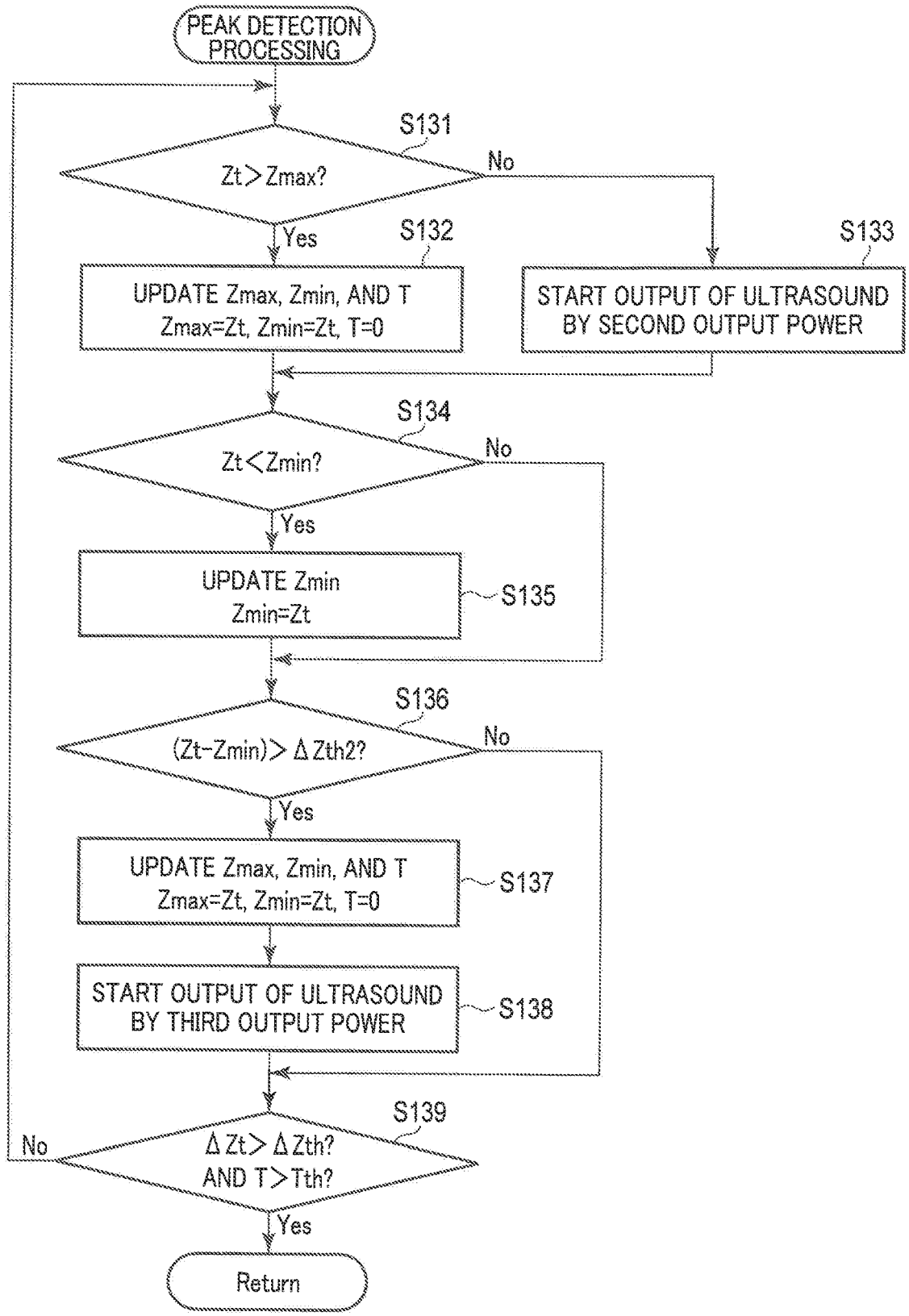
FIG. 9 is a flowchart of an example of peak detection processing.

After step S103, the processor 33 performs ultrasonic impedance peak detection processing (step S104) FIG. 9 is a flowchart of an example of peak detection processing.

In step S131, the determination section 37 of the processor 33 determines whether the ultrasonic impedance Zt is larger than the maximum value Zmax of the ultrasonic impedance. That is, after the elapse of specified time since output of the vibration generation power from the power supply 31 by the first output power, the determination section 37 determines whether the ultrasonic impedance has started gradual decrease. When it is determined that the ultrasonic impedance Zt is larger than the maximum value Zmax (Yes), the processor 33 updates the maximum value Zmax of the ultrasonic impedance to the ultrasonic impedance Zt detected by the property detection section 36 (Zmax=Zt), updates the minimum value Zmin of the ultrasonic impedance to the ultrasonic impedance Zt detected by the property detection section 36, and resets the count time T (T=0) (step S132). Then, the process moves to step S134.

On the other hand, in step S131, when it is determined that the ultrasonic impedance Zt is equal to or less than the maximum value Zmax (No), it means that the ultrasonic impedance Zt has gradually decreased from the peak P1 as illustrated in FIG. 5, for example. Therefore, at a time t11 after the time t1 (immediately after the time t1) at the peak P1 of the ultrasonic impedance illustrated in FIG. 5, the output control section 35 of the processor 33 causes the power supply 31 to start output of electric energy the ultrasonic transducer 22 by second output power (step S133).

In this manner, in the present embodiment, immediately after the detection of gradual decrease of the electrical property value, the output control section 35 causes the power supply 31 to lower the output power to be supplied to the ultrasonic transducer 22. In this case, the elapse of a predetermined time after the detection of a peak of the electrical property value is not used for the determination by the determination section 37. In the present embodiment, based on only the determination by the determination section 37 that the electrical property value has gradually decreased, the output control section 35 causes the power supply 31 to change the output of the electric energy from the first output power to the second output power. In this case, the second output power smaller than the first output power. That is, the output control section 35 causes the power supply 31 to decrease the electric energy to be output to the ultrasonic transducer 22 to decrease the output current from the power supply 31. Therefore, as illustrated in FIG. 5, the value of amplitude of the first gripping piece 14 at the time t11 becomes A11, which is smaller than an amplitude A10 at the times before the time t11. Then, the process moves to step S134.

In step S134, the determination section 37 of the processor 33 determines whether the ultrasonic impedance Zt is smaller than the minimum value Zmin of the ultrasonic impedance. When it is determined that the ultrasonic impedance Zt is smaller than the minimum value Zmin (Yes), the processor 33 updates the minimum value Zmin of the ultrasonic impedance to the ultrasonic impedance Zt detected by the property detection section (Zmin=Zt) (step S135). Then, the process moves to step S136. On the other hand, when it is determined that the ultrasonic impedance Zt is equal to or larger than the minimum value Zmin (No), the process moves to step S136. In this manner, when the ultrasonic impedance Zt is smaller than the minimum value Zmin of the ultrasonic impedance, the maximum value Zmax remains unchanged and the minimum value Zmin is updated, and when it is not so, the maximum value Zmax and the minimum value Zmin are not updated.

In step S136, the determination section 37 of the processor 33 determines whether a gradually increasing value of the ultrasonic impedance Zt from the minimum value Zmin of the ultrasonic impedance, that is, Zt-Zmin is larger than a threshold ΔZth2 as rise detection threshold of the ultrasonic impedance (for example, as illustrated in FIG. 5). The threshold ΔZth2 is a value set in the same manner as the threshold ΔZth1. In step S136, when the determination section 37 of the processor 33 determines that the gradually increasing value Zt-Zmin is equal to or less than the threshold ΔZth2 (No), the process moves to step S139.

On the other hand, in step S136, when the determination section 37 of the processor 33 determines that the gradually increasing value Zt-Zmin is larger than the threshold ΔZth2 (Yes), it means that the ultrasonic impedance Zt has risen from the minimum value Zmin beyond the set value at a time t2 after the time t1, for example, as illustrated in FIG. 5. This indicates that the gripped entire treatment target is not completely cut and divided. Accordingly, the processor 33 updates the maximum value Zmax of the ultrasonic impedance to the ultrasonic impedance Zt detected by the property detection section 36 (Zmax=Zt), updates the minimum value Zmin of the ultrasonic impedance to the ultrasonic impedance Zt detected by the property detection section 36 (Zmin=Zt), and resets the count time T (T=0) (step S137).

Then, to perform an appropriate treatment on the treatment target by the ultrasonic treatment device 2, at the time t2 illustrated in FIG. 5, the output control section 35 of the processor 33 causes the power supply 31 to start output of electric energy to the ultrasonic transducer 22 by third output power (step S138). In this manner, in the present embodiment, when the determination section 37 of the processor 33 determines that the electrical property value has risen again from the minimum value Zmin beyond the set value, the output control section 35 determines that the treatment target will be incised and causes the power supply 31 to increase out power to be supplied, to the ultrasonic transducer 22. That is, the output control section 35 causes tine power supply 31 to change output of the electric energy from the second output power to the third output power. In this case, the third output power is larger than the second output power. That is, the output control section 35 causes the power supply 31 to increase the electric energy to be output to the ultrasonic transducer 22 to increase the output current from the power supply 31. Therefore, as illustrated in FIG. 5, the value of amplitude of the first gripping piece 14 at the time t2 becomes A10, which is larger than the amplitude A11 before the time t2 and after t11.

Referring to FIG. 5, the amplitude value of the first gripping piece 14 making ultrasonic vibration based on the first output power and the amplitude value of the first gripping piece 14 making ultrasonic vibration based on the third output power are approximately identical (both are A10), but these amplitude values may not be identical. As described above, the second output power is smaller than the first output power, and the third output power is larger than the second output power. That is, the first output power may be larger than the third output power, that is, the amplitude value of the first gripping piece 14 before the time t1 may be larger than or smaller than the amplitude value of the first gripping piece 14 after the time t2. After step S138, the process moves to step S139.

In step S139, the determination section 37 of the processor 33 determines whether a gradually decreasing value Zmax−Zt of the ultrasonic impedance Zt from the maximum value Zmax of the ultrasonic impedance, that is, whether a change amount ΔZt is larger than a detection threshold ΔZth as a gradual decrease definite threshold (for example, illustrated in. FIG. 5) (first condition), and determines whether the count time T since the maximum value Zmax starts to be held is larger than a time threshold Tth (for example, illustrated in FIG. 5) (second condition). The detection threshold ΔZth and the time threshold Tth are also set in the same manner as the thresholds ΔZth1 and ΔZth2. In this manner, in step S139, the determination section 37 determines whether the treatment target has been cut and divided by determining whether the ultrasonic impedance Zt has greatly decreased from the last peak value beyond the predetermined value (first condition) and determining whether the time elapsed from the peak value is longer than the predetermined time (second condition).

The first condition and the second condition do not need to be simultaneously satisfied at a certain time t. For example, the determination section 37can determine that the two conditions are satisfied when the gradually decreasing value Zmax−Zt from the maximum value Zmax of the ultrasonic impedance before a certain time t is larger than the threshold ΔZth and when the count time T at the time t is equal to the threshold Tth.

In step S139, when the determination section 37 of the processor 33 determines that at least one of the first condition and the second condition is not satisfied (No), the peak detection processing is not completed. Accordingly, the process returns to step S131. That is, step S131 and the subsequent steps are repeated until the determination section 37 of the processor 33 determines that the treatment target has been cut and divided, that is, that the treatment of the treatment target has completed. For example, in the example illustrated in FIG. 5, step S131 and the subsequent steps are repeated from a time t3 onward after the time t2. Therefore, in step S131, when it is determined that the ultrasonic impedance Zt is equal to or less than the maximum value Zmax (No), it means that the ultrasonic impedance Zt has gradually decreased from the peak P2 as illustrated in FIG. 5, for example. Therefore, at a time t31 after the time t3 (immediately after the time t3) at the peak P2 of the ultrasonic impedance illustrated in FIG. 5, the output control section 35 of the processor 33 causes the power supply 31 to start output of the electric energy to the ultrasonic transducer 22 by the second output power (step S133).

On the other hand, in step S139, when the determination section 37 of the processor 33 determines that the first condition and the second condition are satisfied (Yes), it is determined that the treatment target has been completely cut and divided. Accordingly, the process returns to the main flow and moves to next step S105.

The output control section 35 of the processor 33 controls the output of the power supply 31 and others (step S105). For example, the output control section 35 causes the power supply 31 to automatically stop the output of the electric energy. For example, as illustrated in FIG. 5, at a time t4, when the output control section 35 causes the power supply 31 to stop the output, the first gripping piece 14 also stops ultrasonic vibration. Otherwise, the output control section causes the power supply 31 to further decrease the output of the electric energy from the second output power. Accordingly, the amplitude of the ultrasonic vibration of the first gripping piece 14 in the rod 13 is decreased. Otherwise, the processor 33 transmits a control signal for activation of a notifier 52 to the notifier 52. Accordingly, the notifier 52 makes a notification (an acoustic notification, a visual notification, or combination of the foregoing notifications as described above). The notification may be singly made or may be made in combination with the automatic output stop or output decrease. When the notification is to be singly made, the operator cancels the operation input from the operation button 24 based on this so that the switch 25 turns from the ON state to the OFF state. According to the turning of the switch 25 to the OFF state, the output control section 35 of the processor 33 causes the power supply 31 to stop the output of the electric energy to the ultrasonic transducer 22. After step S105, the flow of treatment is terminated.

In the foregoing description, the processor 33 sets the maximum value Zmax as a peak of the electrical property value and determines the completion of the incision by using the time elapsed from the peak and the gradually decreasing value. Alternatively, the determination on the completion of the incision by using temporal changes in the electrical property value may be made by using the rate of temporal change in the electrical property value or the integrated value of values obtained by subtracting the electrical property value from the peak.

As described above, in the present embodiment, in the flow of treatment by the energy treatment system 1, when the processor 33 detects a peak of the electrical property value including ultrasonic impedance voltage, and electric power, the output control section 35 of the processor 33 immediately causes the power supply 31 to decrease the output of ultrasound, regardless of whether the peak has resulted from cut and separation. That is, when the determination section 37 determines that the electrical property value has started gradual decrease, the output control section 35 causes the power supply 31 to change the vibration generation power from the first output power to the second output power smaller than the first output power. Accordingly, while the first gripping piece 14 is making ultrasonic vibration with a large amplitude and at a high vibration speed, it is possible to prevent the pad 18 of the second gripping piece 15 from being in continuous contact with the first gripping piece 14 in an efficient manner. Therefore, it is possible to prevent the wearing down and deformation of the pad 18 of the second gripping piece 15 in an efficient manner. It is also possible to prevent excessive temperature rise in the first gripping piece 14.

After the lowering of output of ultrasound, when the processor 33 detects again a rise in the electrical property value, the output control section 35 of the processor 33 causes the power supply 31 to increase the output of ultrasound. That is, when the determination section 37 determines that the electrical property value has gradually increased, the output control section 35 causes the power supply 31 to change the vibration generation power from the second output power to the third output power larger than the second output power. According, it is possible to increase again the incision performance of the ultrasonic treatment device 2 that has been decreased by lowering the output of ultrasound. Therefore, the incision of the treatment target can be reliably performed again with high incision performance.

Further, for example, at the time t4 illustrated in FIG. 5, the processor 33 can detect the completion of the incision. Therefore, according to the present embodiment, it is possible to provide the energy treatment system 1 that can reliably determine that the treatment target has been completely cut and divided.

In addition, according to the present embodiment, the output control section 35 of the processor 33 stops the output of the power supply 31 after the complete cut and separation of the treatment target to prevent the treatment target from being left insufficiently cut and divided. According to this as well, while the first gripping piece 14 is making ultrasonic vibration with a large amplitude and at a high vibration speed, it is possible to prevent the pad 18 of the second gripping piece 15 from being in continuous contact with the first gripping piece 14 in an efficient manner. Therefore, it is possible to prevent the wearing down and deformation of the pad 18 of the second gripping piece 15 in an efficient manner.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended clams and their equivalent.

What is claimed is:

1. An energy treatment system comprising:
   a power supply configured to output electric power;
   an ultrasonic transducer configured to generate ultrasonic vibration by the electric power from the power supply;
   a first gripping piece, the ultrasonic transducer being configured to transfer the ultrasonic vibration to the first gripping piece, the first gripping piece being configured to perform a treatment on a treatment target using the ultrasonic vibration;
   a second gripping piece configured to be opened and closed with respect to the first gripping piece; and
   a controller including a processor configured to:
      temporally detect an electrical property value of the ultrasonic transducer;
      after a predetermined time since the power supply outputs the electric power at a first output power, determine that the electrical property value has started a gradual decrease;
      after determining the gradual decrease has started, detect whether the electrical property value has gradually increased;
      when the gradual decrease starts, cause the power supply to output the electric power at a second output power that is smaller than the first output power; and
      after the power supply is configured to output the electric power at the second output power, and when the electrical property value has gradually increased, cause the power supply to output the electric power at a third output power that is larger than the second output power.

2. The energy treatment system according to claim 1, wherein the processor is configured to detect ultrasonic impedance, which is defined as electric impedance of the ultrasonic transducer, as the electric property value.

3. The energy treatment system according to claim 2, wherein when an amount of change in the ultrasonic impedance from a maximum value of the ultrasonic impedance becomes larger than a predetermined amount of change over a predetermined time, the processor is configured to determine that the treatment of the treatment target has been completed, and configured to perform at least one of causing the power supply to stop the electric power or make the electric power lower than the second output power and transmit a notification to an operator of the energy treatment system that the treatment of the treatment target has been completed.

4. The energy treatment system according to claim 2, wherein when an amount of change in the ultrasonic impedance from a minimum value of the ultrasonic impedance becomes larger than a predetermined amount of change, the processor is configured to cause the power supply to change the electric power to the third output power larger than the second output power.

5. The energy treatment system according to claim 1, wherein the processor is configured to detect a value of voltage applied to the ultrasonic transducer, or a value of power supplied to the ultrasonic transducer, as the electric property value.

6. The energy treatment system according to claim 1, wherein the processor is configured to determine that the treatment of the treatment target has completed when the electric property value satisfies a predetermined condition.

7. The energy treatment system according to claim 6, wherein the processor is configured to determine whether the predetermined condition has occurred when the detected electric property value has started the gradual decrease, and a predetermined time has passed since the gradual decrease started.

8. The energy treatment system according to claim 6, further comprising:
   a handpiece comprising the ultrasonic transducer, the first gripping piece, and the second gripping piece; and
   a memory provided on the handpiece or the controller, and configured to store a set value;
   wherein when the handpiece is connected to the controller, the processor is configured to set the predetermined condition based on the set value which is obtained from the memory.

9. The energy treatment system according to claim 6, further comprising an input device configured to receive an instruction from a user; wherein the processor is configured to set the predetermined condition based on the instruction into the input device.

10. The energy treatment system according to claim 1, further comprising an input device configured to receive an instruction from a user, wherein the processor is configured to perform a predetermined action or switch performing or not a predetermined action.

11. The energy treatment system according to claim 1, wherein when the power supply outputs the electric power at the second output power, the first gripping piece is not in continuous contact with the second gripping piece.

12. The energy treatment system according to claim 1, wherein after the power supply is configured to output the electric power at the third output power, and when the electrical property value has gradually decreased, the controller is configured to cause the power supply to output the electric power at the second output power.

13. A method of controlling the electric power output during treatment of the treatment target using the energy treatment system according to claim 1, the method comprising:
- temporally detecting the electrical property value of the ultrasonic transducer;
- after the predetermined time since the power supply outputs the electric power at the first output power, determining that the electrical property value has started the gradual decrease;
- when the gradual decrease starts, changing the electric power from the first output power to the second output power smaller than the first output power;
- detect whether the electrical property value has started the gradual increase; and
- after outputting the electric power at the second output power and when determining that the electrical property value has gradually increased, outputting the electric power at the third output power that is larger than the second output power.

\* \* \* \* \*